US007521006B2

(12) United States Patent
Ikeda et al.

(10) Patent No.: US 7,521,006 B2
(45) Date of Patent: Apr. 21, 2009

(54) DIIMMONIUM COMPOUND AND USE THEREOF

(75) Inventors: Masaaki Ikeda, Kita-ku (JP); Takaaki Kurata, Kita-ku (JP); Syouichi Kaneko, Saitama (JP); Junichi Segawa, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/661,800

(22) PCT Filed: Sep. 2, 2005

(86) PCT No.: PCT/JP2005/016094

§ 371 (c)(1),
(2), (4) Date: Apr. 16, 2007

(87) PCT Pub. No.: WO2006/028006

PCT Pub. Date: Mar. 16, 2006

(65) Prior Publication Data

US 2008/0067478 A1 Mar. 20, 2008

(30) Foreign Application Priority Data

Sep. 6, 2004 (JP) ............................ 2004-258602
Apr. 22, 2005 (JP) ............................ 2005-124368
Apr. 26, 2005 (JP) ............................ 2005-127917

(51) Int. Cl.
*F21V 9/04* (2006.01)

(52) U.S. Cl. ....................... 252/587; 552/302; 524/236; 558/388; 564/271; 359/350; 359/359; 359/360; 359/885; 430/270.11; 313/479

(58) Field of Classification Search ................. 252/587; 552/302; 524/236; 558/388; 564/271; 359/350, 359/359, 360, 885; 430/270.11; 313/479
See application file for complete search history.

(56) References Cited

U.S. PATENT DOCUMENTS 3,575,871 A 4/1971 Susi et al.
4,923,390 A 5/1990 Oguchi et al. ............... 430/270
5,415,957 A * 5/1995 Okada et al. ................ 429/330
5,945,209 A 8/1999 Okazaki et al. .......... 428/304.4
6,475,590 B1 11/2002 Kitayama et al. .......... 428/64.8
6,522,463 B1 * 2/2003 Shimomura et al. ......... 359/350
2002/0033661 A1 * 3/2002 Sugimachi et al. .......... 313/479
2006/0073407 A1 * 4/2006 Yamanobe et al. ....... 430/270.1
2006/0091365 A1 * 5/2006 Kitayama et al. ........... 252/587

FOREIGN PATENT DOCUMENTS

EP 1 090 910 4/2001
EP 1 176 436 1/2002
EP 1 403 666 3/2004
EP 1 496 375 1/2005
EP 1 564 260 8/2005
EP 1 589 358 10/2005
JP 64-38490 2/1989
JP 10-180922 7/1998
JP 10-180947 10/1998
JP 2000-211239 * 2/2000
JP 2000-81511 3/2000
JP 2000-211239 * 8/2000
JP 2000-227515 8/2000
JP 2000-229931 8/2000
JP 2001-175185 6/2001

(Continued)

OTHER PUBLICATIONS

The European Search Report dated Aug. 13, 2008.

*Primary Examiner*—Lorna M Douyon
*Assistant Examiner*—Bijan Ahvazi
(74) *Attorney, Agent, or Firm*—Nields & Lemack

(57) ABSTRACT

Disclosed is a near-infrared absorbing compound which does not contain antimony or arsenic, and has excellent stability, especially excellent heat resistance, light resistance and moist heat resistance. Also disclosed are a near-infrared absorbing filter, which is produced by using the near-infrared absorbing compound, and has excellent resistance such as light resistance and heat resistance, an optical filter and an optical recording medium. Specifically disclosed are a diimmonium compound represented by the formula (1) below and a near-infrared absorbing filter obtained by using such a diimmonium compound. Further specifically disclosed are a near-infrared absorbing filter wherein an adhesive layer containing the diimmonium compound is arranged on a transparent supporting body, and an optical filter using such a near-infrared absorbing filter.

(1)

(In the formula (1), $R_1$ to $R_8$ independently represent a hydrogen atom or an optionally substituted aliphatic hydrocarbon residue; $R_9$ to $R_{11}$ independently represent an aliphatic hydrocarbon residue which may have a halogen atom; and rings A and B may further have a substituent).

21 Claims, No Drawings

U.S. PATENT DOCUMENTS

| | | |
|---|---|---|
| JP | 2005-49848 | 2/2005 |
| TW | 173937 | 12/1991 |
| TW | 335435 | 7/1998 |
| TW | 454009 | 9/2001 |
| WO | 99/67200 | 12/1999 |
| WO | 03/005076 | 1/2003 |
| WO | 2004/048480 | 6/2004 |
| WO | 2004/068199 | 8/2004 |

* cited by examiner

DIIMMONIUM COMPOUND AND USE THEREOF

TECHNICAL FIELD

The present invention relates to a compound having absorption in a near-infrared region and the use thereof. The present invention particularly relates to a diimmonium compound which is not a deleterious substance and is superior in heat resistance, light resistance and solubility, a near-infrared light absorbing filter using the diimmonium compound, and an optical filter and an optical information recording medium using the diimmonium compound.

BACKGROUND ART

A diimmonium compound as a near-infrared light absorbing material has been widely known (for instance, see Patent Documents 1 to 3), and has been widely used in a near-infrared light absorbing filter, a thermal insulation film, sunglasses and the like. However, among these compounds, the compounds having a hexafluoroantimonate ion, a hexafluoroarsenate ion or the like as a counter ion has been used for the reason of being comparatively superior in heat resistance, and above all, the compound having a hexafluoroantimonate ion as a counter ion has been used in many cases. However, a compound not containing these metals has been desired to be developed in the industrial field in which the use of heavy metals is regulated, particularly, in the field of electric material, because the compound containing antimony is categorized as a deleterious substance. As means for solving the problem, there is a method of using a perchlorate ion, a hexafluorophosphate ion and a fluoroborate ion as the counter ion, but these counter ions are insufficient, in consideration of heat resistance and resistance to moist heat. Furthermore, a compound using an organic counter ion such as naphthalenedisulfonic acid is proposed (for instance, see Patent Document 2), but a field in which the compound is practically usable is limited because molar absorptivity is low and the compound in itself takes on a green tinge. In addition, compounds using a trifluoromethanesulfonate ion, bis(trifluoromethane)sulfonic acid imide and the like have been known (for instance, see Patent Documents 1, 4 and 5), but it cannot be said that these compounds have sufficient heat resistance and resistance to moist heat, so that a more excellent compound has been demanded to be developed.

By the way, near-infrared light is used for a beam for remotely operating electrical machinery and apparatuses, so that machinery and apparatuses emitting near-infrared light may cause misoperation in electrical machinery and apparatuses installed in the periphery. It is therefore needed to install a filter having a function of shielding near-infrared light on the front surface of such machinery and apparatuses.

Among electrical machinery and apparatuses, a PDP (plasma display, panel) has been frequently used in large-sized televisions in recent years. The PDP generates visible light necessary for an image according to a principle of: applying voltage on a rare gas (such as neon and xenon) which is sealed in a cell sandwiched between two pieces of tabular glass to generate ultra-violet light; and making the generated ultra-violet light irradiate a luminous body coated on the surface of cell wall. However, the PDP also emits a harmful electromagnetic wave such as near-infrared light, an electromagnetic wave harmful to a human body and an orange beam (hereafter referred to as neon light) which is originated in neon gas and decreases red light, simultaneously with the emission of visible light. It is accordingly needed to equip the PDP with an optical filter which passes the useful visible light through itself but shields the harmful electromagnetic wave including the near-infrared light.

A near-infrared light absorbing filter to be used in an optical filter is produced by coating a compound which absorbs near-infrared light (a near-infrared light absorbing compound) on the surface of a transparent support or on the surface of a functional film such as a film for shielding an electromagnetic wave which is harmful to a human body (hereafter referred to as an electromagnetic-wave-shielding film) with the use of a polymer resin as a binder. There are many near-infrared light absorbing compounds in such a field of application, but a diimmonium compound or a combination thereof with another near-infrared light absorbing compound is often used because a diimmonium compound has a wide absorption wavelength region to the near-infrared light.

However, a conventional diimmonium compound has not only the disadvantage of the harmfulness as above described, but also has a problem on stability as has been pointed out that the diimmonium compound has insufficient stability on heat resistance and on resistance to moist heat in general, when a near-infrared light absorbing filter is prepared by coating the diimmonium compound on a resin film with the use of a resin as a binder.

Patent Document 6 discloses a technology for stabilizing a diiummonium compound by making a polymeric resin layer contain the diimmonium compound while controlling the amount of a solvent remaining in the resin layer to a specified ratio or smaller. The technology needs, however, some work of controlling the amount of the remaining solvent, so that a diimmonium compound has been desired to be developed which shows high heat resistance and resistance to moist heat when coated by a more general coating method and drying method. Patent Document 7 discloses an optical filter with near-infrared light absorptivity, which has a diimmonium compound with a bis(fluoroalkyl sulfonyl) imide anion or a tris(fluoroalkyl sulfonyl)carbanion contained in a coating layer of a transparent polymeric resin, and states that the diimmonium compound, particularly one having the bis(fluoroalkyl sulfonyl)imide anion, shows good heat resistance and resistance to moist heat with specific examples of the compound. However, the Patent Document does not describe the name of a specific compound, a specific production method, physical properties or an application example about the diimmonium compound having the tris(fluoroalkyl sulfonyl) carbanion. Further, there is a method of making a near-infrared light absorbing compound contained in a sticking layer for adhesively bonding a polymeric resin film to a support, as a method of making a near-infrared light absorbing compound held in a resin film. The method can make the near-infrared light absorbing compound contained in the sticking layer of a functional film such as an anti-reflection film and an electromagnetic-wave-shielding film which compose an optical filter, and accordingly has a great merit of cost reduction in comparison with the method of additionally forming a layer containing the near-infrared light absorbing compound, because one step can be eliminated from coating steps. However, the method has been considered to have a high technical hurdle because of aggravating heat resistance and resistance to moist heat more than the method of making the near-infrared light absorbing compound contained in a polymeric resin film or in a coating layer.

Patent Document 1: Japanese Patent Publication (KOKOKU) No. 07-51555 (Page 2)

Patent Document 2: Japanese Patent Laying Open (KOKAI) No. 10-316633 (Page 5)

Patent Document 3: Japanese Patent Publication (KOKOKU) No. 43-25335 (Pages 7 to 14)

Patent Document 4: International Publication Pamphlet WO2004/068199

Patent Document 5: International Publication Pamphlet WO2004/048480

Patent Document 6: Japanese Patent Laying Open (KOKAI) No. 2000-227515

Patent Document 7: Japanese Patent Laying Open (KOKAI) No. 2005-49848 (Pages 2 to 12)

DISCLOSURE OF THE INVENTION

Problems to be Solved by the Invention

The present invention is developed under the above described situation. An object of the present invention is to provide a near-infrared light absorbing compound which does not contain a heavy metal such as antimony, and has more excellent stability, particularly, heat resistance, light resistance and resistance to moist heat; such a near-infrared light absorbing filter (particularly for a plasma display panel); and further a photorecording medium and a resin composition superior in atmospheric corrosion resistance. Another object of the present invention is to provide a particularly preferred embodiment of the near-infrared light absorbing filter using the diimmonium compound according to the present invention.

Means of Solving the Problems

As a result of making an extensive investigation for solving the above described problems, the present inventors found that a diimmonium compound having a particular structure solves the above described various problems, and arrived at the accomplishment of the present invention. Specifically, the present invention relates to:

(1) a diimmonium compound represented by the following Formula (1):

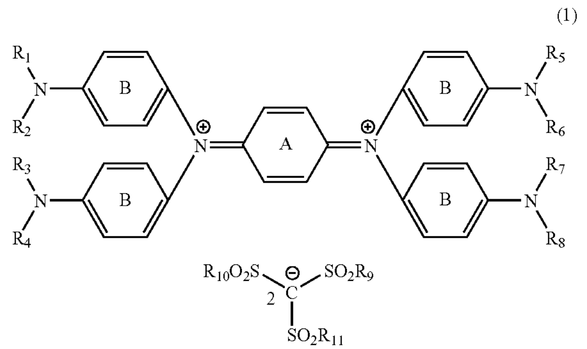

(wherein $R_1$ to $R_8$ each independently represent a hydrogen atom or an aliphatic hydrocarbon residue which may have a substituent; $R_9$ to $R_{11}$ each independently represent an aliphatic hydrocarbon residue which may have a halogen atom; and rings (A) and (B) may independently have a further substituent);

(2) the diimmonium compound according to the item (1), wherein the diimmonium compound shown by Formula (1) is a compound represented by the following Formula (2):

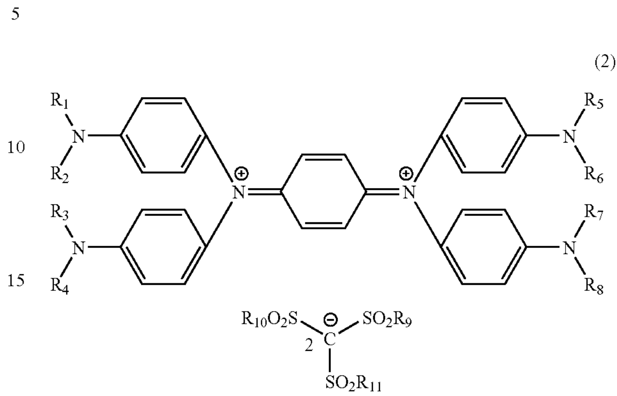

(wherein $R_1$ to $R_8$ and $R_9$ to $R_{11}$ have the same meanings as described for Formula (1));

(3) the diimmonium compound according to items (1) or (2), wherein all of $R_9$ to $R_{11}$ in Formula (1) are aliphatic hydrocarbon residues having a fluorine atom;

(4) the diimmonium compound according to the item (3), wherein the aliphatic hydrocarbon residue having a fluorine atom is a trifluoromethyl group;

(5) the diimmonium compound according to any one of items (1) to (4), wherein all of $R_1$ to $R_8$ in Formula (1) are straight chain or branched chain alkyl groups;

(6) the diimmonium compound according to the item (5), wherein the straight chain or branched chain alkyl group is a $C_1$ to $C_6$ straight chain or branched chain alkyl group;

(7) the diimmonium compound according to the item (6), wherein the straight chain or branched chain alkyl group is a $C_2$ to $C_5$ straight chain or branched chain alkyl group;

(8) the diimmonium compound according to the item (7), wherein the straight chain or branched chain alkyl group is an ethyl group, an n-propyl group, an n-butyl group, an iso-butyl group or an n-amyl group;

(9) the diimmonium compound according to any one of items (1) to (4), wherein the substituents in aliphatic hydrocarbon residues which may have a substituent of $R_1$ to $R_8$ in Formula (1) or Formula (2) are each independently a halogen atom, a cyano group, a nitro group, a hydroxyl group, a carboxyl group, a carbonamide group, an alkoxycarbonyl group, an acyl group, an aryl group or an alkoxyl group;

(10) the diimmonium compound according to the item (9), wherein all of $R_1$ to $R_8$ are alkyl groups substituted by a cyano group;

(11) the diimmonium compound according to the item (10), wherein the alkyl group substituted by a cyano group is a cyanopropyl group;

(12) a resin composition characterized by comprising the diimmonium compound according to any one of items (1) to (11) and a resin;

(13) a near-infrared light absorbing filter characterized by having a layer comprising the diimmonium compound according to any one of items (1) to (11);

(14) the near-infrared light absorbing filter according to the item (13), wherein the layer comprising the diimmonium compound is a sticking layer;

(15) the near-infrared light absorbing filter according to the item (14), wherein the sticking layer comprises a rust-preventing agent;

(16) the near-infrared light absorbing filter according to the item (15), wherein the rust-preventing agent is 1H-benzotriazole;

(17) the near-infrared light absorbing filter according to any one of items (14) to (16), wherein the content of an organic acid in the sticking layer is 0.5 mass % or less with respect to the mass of the sticking layer;

(18) the near-infrared light absorbing filter according to any one of items (14) to (17), characterized in that the sticking layer comprises a compound having the absorption maximum in a wavelength between 550 and 620 nm together with the diimmonium compound of Formula (1);

(19) an optical filter for a plasma display panel characterized by comprising the near-infrared light absorbing filter according to any one of items (13) to (18) and an electromagnetic-wave-shielding layer;

(20) a plasma display panel having the optical filter for a plasma display panel according to the item (19); and

(21) an optical information recording medium characterized by comprising a recording layer containing the diimmonium compound according to any one of items (1) to (11).

Effect of the Invention

The diimmonium compound having near-infrared light absorbing properties according to the present invention is a compound which does not include antimony and arsenic, is not a deleterious substance, has molar absorptivity as high as 100,000 or higher, is superior in heat resistance and light resistance, and has high solubility. The diimmonium compound is particularly superior in heat resistance and resistance to moist heat to a conventional diimmonium compound containing a hexafluorophosphate ion, a perchlorate ion or a fluoroborate ion. Because of having such characteristics, the diimmonium compound according to the present invention can be preferably used as a material for absorbing near-infrared light such as in a near-infrared light absorbing filter, a thermal insulation film and sunglasses, and is particularly preferable for the near-infrared light absorbing filter for a plasma display.

A near-infrared light absorbing filter using a diimmonium compound according to the present invention adequately absorbs near-infrared light in a wavelength region of 700 to 1,100 nm. Particularly, when having the diimmonium compound contained in a sticking layer which is provided on a transparent support, the near-infrared light absorbing filter shows excellent heat resistance and resistance to moist heat, and does not cause the degradation of near-infrared light absorptivity, the discoloration of the layer and the degradation of surface quality. Accordingly, an optical filter for a PDP, which is formed by combining the near-infrared light absorbing filter and another functional film, shows excellent performance and can sufficiently cope with the above described problems.

Furthermore, an optical information recording medium according to the present invention can have greatly improved light resistance in comparison with an optical information recording medium containing a conventional diimmonium compound. In addition, the diimmonium compound according to the present invention has sufficient solubility in preparing the optical information recording medium, and has superior workability as well. In addition, when making the compound contained, for instance, in a thin film of an organic coloring matter, which is a recording layer of the optical information recording medium, the provided optical information recording medium shows remarkably improved durability and stability of light resistance in a re-recording operation.

BEST MODE FOR CARRYING OUT THE INVENTION

The diimmonium compound according to the present invention is a salt composed of one particular diimmonium cation and two particular anions as counter ions, and is represented by the following Formula (1).

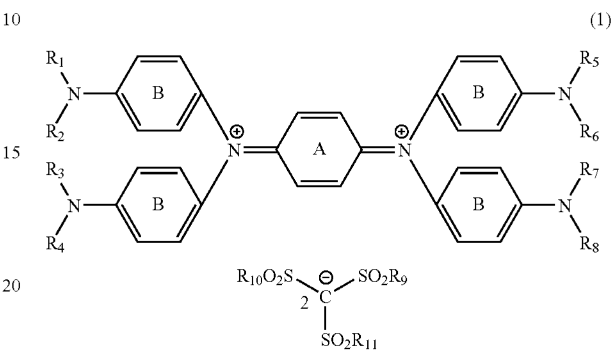

In Formula (1), $R_9$ to $R_{11}$ each independently represent an aliphatic hydrocarbon residue which may have a halogen atom. The aliphatic hydrocarbon residue includes saturated and unsaturated, straight chain, branched chain and cyclic alkyl groups of preferably having 1 to 36 carbon atoms; is more preferably saturated straight chain alkyl groups which may have a substituent and have 1 to 20 carbon atoms; and is most preferably the above alkyl group having 1 to 4 carbon atoms. The halogen atom is preferably a fluorine, chlorine, bromine or iodine atom; is more preferably a fluorine, chlorine or bromine atom; and is most preferably a fluorine atom. A specific example of the group includes: a saturated straight chain alkyl group such as a methyl group, a trifluoromethyl group, a difluoromethyl group, a monofluoromethyl group, a dichloromethyl group, a monochloromethyl group, a dibromomethyl group, a difluorochloromethyl group, an ethyl group, a pentafluoroethyl group, a tetrafluoroethyl group, a trifluoroethyl group, a trifluorochloroethyl group, a difluoroethyl group, a monofluoroethyl group, a trifluoroiodoethyl group, a propyl group, a heptafluoropropyl group, a hexafluoropropyl group, a pentafluoropropyl group, a tetrafluoropropyl group, a trifluoropropyl group, a difluoropropyl group, a monofluoropropyl group, a perfluorobutyl group, a perfluorohexyl group, a perfluorooctyl group and a perfluorooctylethyl group; an unsaturated alkyl group such as an allyl group, a tetrafluoroallyl group, a trifluorovinyl group and a perfluorobutylvinyl group; a branched chain alkyl group such as an isopropyl group, a pentafluoroisopropyl group, a heptafluoroisopropyl group, a perfluoro-3-methylbutyl group and a perfluoro-3-methylhexyl group; and a cyclic alkyl group such as a cyclohexyl group. In Formula (1), $R_9$ to $R_{11}$ are preferably all the same. Further, all of $R_9$ and $R_{10}$, $R_9$ and $R_{11}$ or $R_{10}$ and $R_{11}$ may be coupled to form a cyclic alkyl group.

It is particularly preferable that all of $R_9$ to $R_{11}$ are aliphatic hydrocarbon residues having a fluorine atom. A specific example of the residue includes a trifluoromethyl group, a difluoromethyl group, a monofluoromethyl group, a pentafluoroethyl group, a tetrafluoroethyl group, a trifluoroethyl group, a difluoroethyl group, a heptafluoropropyl group, a hexafluoropropyl group, a pentafluoropropyl group, a tetrafluoropropyl group, a trifluoropropyl group and a perfluorobutyl group; is preferably a trifluoromethyl group, a difluoromethyl group, a pentafluoroethyl group, a trifluoroethyl group, a heptafluoropropyl group, a tetrafluoropropyl group and a perfluorobutyl group; and more preferably is a trifluoromethyl group. In the above described respective groups, an alkyl moiety is straight chain unless otherwise specified.

In Formula (1), rings (A) and (B) may respectively have 1 to 4 substituents in positions other than 1-position and 4-position. The substituent that may be bonded includes, for instance, a halogen atom, a hydroxyl group, a lower alkoxy group, a cyano group and a lower alkyl group. The halogen atom includes, for instance, a fluorine atom, a chlorine atom, a bromine atom and an iodine atom. The lower alkoxy group includes, for instance, a C1 to C5 alkoxy group such as a methoxy group and an ethoxy group, and the lower alkyl group includes, for instance, a C1 to C5 alkyl group such as a methyl group and an ethyl group. It is preferable in Formula (1) that any of rings (A) and (B) does not have a substituent in positions except 1-position and 4-position, or both of the rings (A) and (B) are substituted by a halogen atom (a chlorine atom, a bromine atom and a fluorine atom in particular), a methyl group or a cyano group.

When a ring (B) has a substituent, all of the four rings (B) preferably have the same substituents, and furthermore, the substituent is preferably bonded to an m-position with respect to a nitrogen atom bonded to the ring (A).

$R_1$ to $R_8$ each independently represent a hydrogen atom or an aliphatic hydrocarbon residue which may have a substituent. The aliphatic hydrocarbon residue means a group formed by eliminating one hydrogen atom from a saturated or unsaturated, straight chain, branched chain or cyclic aliphatic hydrocarbon. The number of carbon atoms is 1 to 36, and preferably is 1 to 20.

A specific example of a saturated aliphatic hydrocarbon residue or an unsaturated aliphatic hydrocarbon residue having no substituent group includes a methyl group, an ethyl group, an n-propyl group, an iso-propyl group, an n-butyl group, an iso-butyl group, an s-butyl group, a ter-butyl group, an n-pentyl group, an iso-pentyl group, a ter-pentyl group, an octyl group, a decyl group, a dodecyl group, an octadecyl group, an isopropyl group, a cyclopentyl group, a cyclohexyl group, a vinyl group, an allyl group, a propenyl group, a pentynyl group, a butenyl group, a hexenyl group, a hexadienyl group, an isopropenyl group, an isohexenyl group, a cyclohexenyl group, a cyclopentadienyl group, an ethynyl group, a propynyl group, a hexynyl group, an isohexynyl group and a cyclohexynyl group. Among those, a preferred residue includes a C1 to C5 saturated aliphatic straight chain or branched chain hydrocarbon residue or an unsaturated aliphatic hydrocarbon residue, such as a methyl group, an ethyl group, an n-propyl group, an iso-propyl group, an n-butyl group, an iso-butyl group, a sec-butyl group, a ter-butyl group, an n-pentyl group, an iso-pentyl group, a ter-pentyl group, a vinyl group, an allyl group, a propenyl group and a pentynyl group.

In the present invention, all of $R_1$ to $R_8$ are preferably a straight chain or branched chain alkyl group, and more preferably are a (C2-C5) straight chain or branched chain alkyl group. A specific example of the particularly preferred straight chain or branched chain alkyl group includes an ethyl group, an n-propyl group, an n-butyl group, an iso-butyl group, and an n-amyl group.

An example of a substituent in an aliphatic hydrocarbon residue having a substituent includes, for instance: a halogen atom (such as F, Cl and Br), a hydroxyl group, an alkoxy group (such as a methoxy group, an ethoxy group and an isobutoxy group), an alkoxyalkoxy group (such as a methoxyethoxy group), an aryl group (such as a phenyl group and a naphthyl group; and the aryl group may further have a substituent), an aryloxy group (such as a phenoxy group), an acyloxy group (such as an acetyloxy group, a butyryloxy group, a hexylyloxy group and a benzoyloxy group; and the aryloxy group may further have a substituent), an amino group, an alkyl substituted amino group (such as a methylamino group and a dimethylamino group), a cyano group, a nitro group, a carboxyl group, a carbonamide group, an alkoxycarbonyl group (such as a methoxycarbonyl group and an ethoxycarbonyl group), an acyl group, an amide group (such as an acetamido group), a sulfonamide group (such as a methane sulfonamide group), and a sulfo group. Among those substituents, a preferred substituent is a halogen atom, a cyano group, a nitro group, a hydroxyl group, a carboxyl group, a carbonamide group, an alkoxycarbonyl group, an acyl group, an aryl group or an alkoxyl group.

A specific example of an aliphatic hydrocarbon residue having a substituent includes: a cyano substituted (C1-C6) alkyl group such as a cyanomethyl group, a 2-cyanoethyl group, a 3-cyanopropyl group, a 2-cyanopropyl group, a 4-cyanobutyl group, a 3-cyanobutyl group, a 2-cyanobutyl group, a 5-cyanopentyl group, a 4-cyanopentyl group, a 3-cyanopentyl group, a 2-cyanopentyl group and 3,4-dicyanobutyl group; an alkoxy substituted (C1-C6) alkyl group such as a methoxyethyl group, an ethoxyethyl group, a 3-methoxypropyl group, a 3-ethoxypropyl group, a 4-methoxybutyl group, a 4-ethoxybutyl group, a 5-ethoxypentyl group and a 5-methoxypentyl group; and fluorinated (C1-C8) alkyl group such as a trifluoromethyl group, a monofluoromethyl group, a pentafluoroethyl group, a tetrafluoroethyl group, a trifluoroethyl group, a heptafluoropropyl group, a perfluorobutyl group, a perfluorobutylethyl group, a perfluorohexyl group, a perfluorohexylethyl group, a perfluorooctyl group and a perfluorooctylethyl group.

A preferred example of an aliphatic hydrocarbon residue having a substituent includes an alkyl group substituted by a cyano group. An example of a preferred diiummonium compound includes: a diimmonium compound in which all of $R_1$ to $R_8$ are an alkyl group substituted by a cyano group; and a diimmonium compound in which at least one of $R_1$ to $R_8$ is an alkyl group substituted by a cyano group. Here, the specific example of the alkyl group substituted by a cyano group includes a cyanopropyl group.

In a diimmonium compound in Formula (1), $R_1$ to $R_8$ can be independent from each other. For instance, one amino group may be substituted by an unsubstituted straight chain alkyl group and a cyano substituted alkyl group; by an unsubstituted branched chain alkyl group and a cyano substituted alkyl group; or by an unsubstituted straight chain alkyl group and an unsubstituted branched chain alkyl group.

Among diimmonium compounds shown by Formula (1) in the present invention, a preferred example of the compound includes a compound shown by Formula (2).

(2)

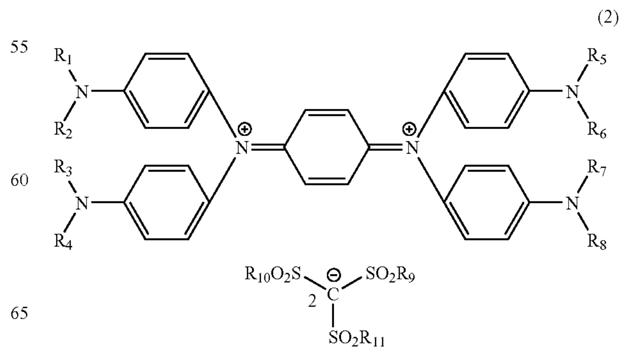

In Formula (2), $R_1$ to $R_8$ and $R_9$ to $R_{11}$ represent the same meaning as in the description for Formula (1).

A diimmonium compound shown by Formula (1) according to the present invention can be obtained by a method in conformance to a method described in Patent Document 3. Specifically, the product of Ullmann reaction between p-phenylenediamins and 1-chloro-4-nitrobenzenes is reduced to obtain a compound represented by the following Formula (3):

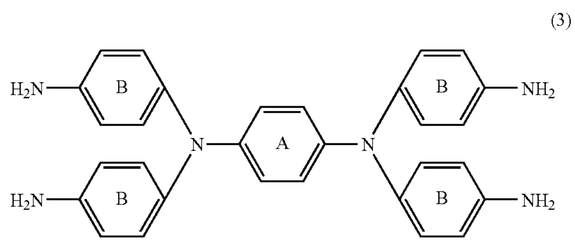

(In Formula (3), rings (A) and (B) have the same meanings as described for the above described Formula (1)).

Then the compound represented by Formula (3) is reacted with a halogenated compound corresponding to the desired $R_1$ to $R_8$ (for instance, n-$C_4H_9Br$ when all of $R_1$ to $R_8$ are n-$C_4H_9$), in an organic solvent, preferably in a water-soluble polar solvent such as dimethylformamide (DMF), dimethyl imidazolidinone (DMI) and N-methylpyrrolidone (NMP) at 30 to 160° C., preferably at 50 to 140° C. to obtain a compound represented by the following Formula (4) in which all of substituents $R_1$ to $R_8$ are the same. Alternatively, when preparing a compound represented by the following Formula (4) (for instance, a precursor of a compound with a compound No. 19 which will be described later) other than a compound represented by Formula (4) in which all substituents $R_1$ to $R_8$ are the same, an n-butyl group is first introduced into four groups among $R_1$ to $R_8$ by reacting the compound represented by Formula (3) with a reagent (n-$C_4H_9Br$) of predetermined moles (for instance, 4 moles per one mole of the Formula (3)), and then the obtained compound is reacted with a reagent (iso-$C_4H_9Br$) necessary for introducing the remaining substituents (iso-butyl group) in an amount of necessary moles (for instance, 4 moles per one mole of an amine compound in the Formula (4)) to prepare the compound represented by Formula (4). Still alternatively, when preparing the other arbitrary compounds than the above described compounds, a similar method as in the method for preparing the compound in exemplified No. 19 is conducted.

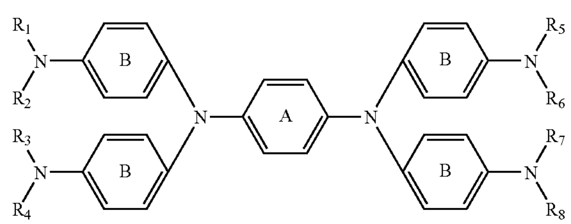

Then the compound shown by Formula (4) which has been obtained as described above, is subjected to an oxidation reaction by adding an oxidizing agent (such as silver salt) corresponding to the following Formula (5) in an amount of 2 equivalents in an organic solvent, preferably, in a water-soluble polar solvent such as DMF, DMI and NMP, at 0 to 100° C., preferably at 5 to 70° C. to obtain a diimmonium compound represented by the Formula (1). Alternatively, the compound shown by Formula (4) which has been obtained as described above is oxidized with an oxidizing agent such as silver nitrate, silver perchlorate and cupric chloride, and then is subjected to salt exchange by adding an acid or a salt having an anion shown by Formula (5) to the reacted liquid to obtain a diimmonium compound represented by the Formula (1). Still alternatively, an acid or an alkaline metal salt containing the anion shown by Formula (5) is added to the compound shown by Formula (4) which has been obtained as described above, and then the oxidizing agent of mineral acid such as the above described silver nitrate and silver perchlorate is added to the product to cause an oxidation reaction to obtain a diimmonium compound represented by the Formula (1).

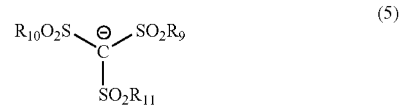

A specific example of a diimmonium compound according to the present invention shown by Formula (1) will be shown in the following Table 1. In the column concerning $R_1$ to $R_8$ of the table, n- is an abbreviation of "normal" and means a straight chain, i- is an abbreviation of "iso-" and means a branched chain, and cy means "cyclo". In the column concerning rings (A) and (B), the case when positions other than 1-position and 4-position are unsubstituted is expressed by "4H", and a substituted position is a position with respect to a nitrogen atom bonded to the ring (A). In addition, in the column concerning $R_1$ to $R_8$, when all of $R_1$ to $R_8$ are n-butyl groups, the formula is abbreviated as "4(n-$C_4H_9$, n-$C_4H_9$)", and, for instance, when one is an iso-pentyl group and the others are an n-butyl group, in other words, when one of four combinations of substituents is the iso-pentyl group and all of the other three combinations are the n-butyl groups, the formula is abbreviated as "3(n-$C_4H_9$, n-$C_4H_9$),(n-$C_4H_9$, i-$C_5H_{11}$)". In addition, in the column concerning $R_9$ to $R_{11}$, all of alkyl moieties having 3 or more carbon atoms are formed of a straight chain.

TABLE 1

Specific example of diimmonium compund

| Cpd No. | $(R_1, R_2)(R_3, R_4)$ $(R_5, R_6)(R_7, R_8)$ | A | B | $R_9$ | $R_{10}$ | $R_{11}$ |
|---|---|---|---|---|---|---|
| 1 | 4 (n-$C_4H_0$, n-$C_4H_9$) | 4H | 4H | $CF_3$ | $CF_3$ | $CF_3$ |
| 2 | 4 (i-$C_4H_9$, i-$C_4H_9$) | 4H | 4H | $CF_3$ | $CF_3$ | $CF_3$ |
| 3 | 4 ($C_3H_6CN$, $C_3H_6CN$) | 4H | 4H | $CF_3$ | $CF_3$ | $CF_3$ |
| 4 | 4 (i-$C_5H_{11}$, i-$C_5H_{11}$) | 4H | 4H | $CF_3$ | $CF_3$ | $CF_3$ |
| 5 | 4 (n-$C_5H_{11}$, n-$C_5H_{11}$) | 4H | 4H | $CF_3$ | $CF_3$ | $CF_3$ |
| 6 | 4 (i-$C_5H_{11}$, n-$C_5H_{11}$) | 4H | 4H | $CF_3$ | $CF_3$ | $CF_3$ |
| 7 | 4 ($C_2H_4OCH_3$, $C_2H_4OCH_3$) | 4H | 4H | $CF_3$ | $CF_3$ | $CF_3$ |
| 8 | 4 ($CH_2CH{=}CH_2$, $CH_2CH{=}CH_2$) | 4H | 4H | $CF_3$ | $CF_3$ | $CF_3$ |
| 9 | 4 ($C_4H_8CN$, $C_4H_8CN$) | 4H | 4H | $CF_3$ | $CF_3$ | $CF_3$ |
| 10 | 4 (n-$C_3H_7$, i-$C_3H_7$) | 4H | 4H | $CF_3$ | $CF_3$ | $CF_3$ |
| 11 | 4 (i-$C_4H_9$, $C_3H_0CN$) | 4H | 4H | $CF_3$ | $CF_3$ | $CF_3$ |
| 12 | 4 (Cy-$C_6H_{11}$, n-$C_6H_{11}$) | 4H | 4H | $CF_3$ | $C_2F_5$ | $CF_3$ |
| 13 | 4 (n-$C_4H_9$, n-$C_4H_9$) | 4H | 4H | $C_2F_5$ | $C_2F_5$ | $C_2F_5$ |
| 14 | 4 (n-$C_4II_0$, n-$C_4II_0$) | 4H | 4H | $C_3F_7$ | $C_3F_7$ | $C_3F_7$ |
| 15 | 4 (n-$C_4H_9$, n-$C_4H_9$) | 4H | 3-$CH_3$ | $CF_3$ | $CF_3$ | $CF_3$ |
| 16 | 4 ($CF_3$, $CF_3$) | 4H | 3-Br | $CF_3$ | $CF_3$ | $CF_3$ |
| 17 | 4 ($CF_2CF_3$,$CF_2CF_3$) | 4H | 4H | $CF_3$ | $C_2F_5$ | $CF_3$ |
| 18 | 4 (n-$C_3F_7$, n-$C_3F_7$) | 4H | 4H | $CF_3$ | $CF_3$ | $CF_3$ |
| 19 | 4 (n-$C_4H_9$, i-$C_4H_9$) | 4H | 4H | $CF_3$ | $CF_3$ | $CF_3$ |
| 20 | 3 (n-$C_4H_9$, n-$C_4H_9$) 1 (n-$C_4H_9$, i-$C_5H_{11}$) | 4H | 4H | $CF_3$ | $CF_3$ | $CF_3$ |
| 21 | 4 ($C_2H_5$, $C_2H_5$) | 4H | 4H | $CF_3$ | $CF_3$ | $CF_3$ |
| 22 | 4 ($C_3H_6CF_3$, $C_3H_6CF_3$) | 4H | 4H | $CF_3$ | $CF_3$ | $CF_3$ |
| 23 | 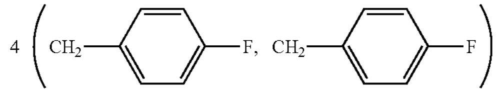 | 4H | 4H | $CF_3$ | $CF_3$ | $CF_3$ |
| 24 | 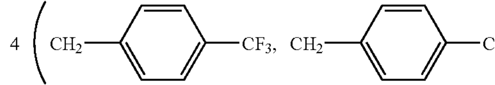 | 4H | 4H | $CF_3$ | $CF_3$ | $CF_3$ |
| 25 | 4 ($CH_2$–$C_6H_2(CF_3)_3$, $CH_2$–$C_6H_2(CF_3)_3$) | 4H | 4H | $CF_3$ | $CF_3$ | $CF_3$ |
| 26 | 4 (n-$C_3H_7$, n-$C_3H_7$) | 4H | 4II | $CF_3$ | $CF_3$ | $CF_3$ |

A resin composition according to the present invention contains a resin and a diimmonium compound shown in Formula (1) according to the present invention.

A specific example of a resin to be used in a resin composition according to the present invention includes: an addition polymer of a vinyl compound such as polyethylene, polystyrene, polyacrylic acid, polyacrylate, polyvinyl acetate, polyacrylonitrile, polyvinyl chloride and polyvinyl fluoride; polymethacrylic acid, polymethacrylate, polyvinylidene chloride, polyvinylidene fluoride, polyvinylidene cyanide, a copolymer of a vinyl compound or a fluorine-based compound such as vinylidene fluoride/trifluoroethylene copolymer, vinylidene fluoride/tetrafluoroethylene copolymer and vinylidene cyanide/vinyl acetate copolymer; a fluorine-containing resin such as polytrifluoroethylene, polytetrafluoroethylene and polyhexafluoropropylene; polyamide like nylon 6 and nylon 66, polyimide, polyurethane, polypeptide, a polyester such as polyethylene terephthalate; polycarbonate, a polyether such as polyoxymethylene; an epoxy resin, polyvinyl alcohol and polyvinylbutyral.

The method of producing a resin composition according to the present invention and the method of using the same is not limited in particular, but a method well-known in itself can be employed, for instance, as followings:

(1) a method of kneading a resin with a diimmonium compound according to the present invention, heating it and molding it to produce a resin plate or a film;

(2) a method of cast-polymerizing the diimmonium compound according to the present invention with a resin monomer or a prepolymer of the resin monomer in the presence of a polymerization catalyst to produce a resin plate or a film;

(3) a method of preparing a paint containing the resin composition according to the present invention, and coating the paint onto a transparent resin plate, a transparent film or a transparent glass plate;

(4) a method of producing a laminated resin plate, a laminated resin film or a laminated glass plate using a resin composition (sticking agent) containing a diiummonium compound according to the present invention and a resin (sticking material); and (5) a method of forming a sticking layer formed of a sticking agent containing the diimmonium compound according to the present invention on the surface of a transparent support (when the transparent support has the above described function, on the surface of the side which does not hinder the function), in a step of coating the sticking agent, and making the sticking layer retain the diimmonium compound.

The above described production method (1) ordinarily includes, though a treatment temperature and a film-forming (resin-plate-forming) condition vary according to a resin (base resin) to be used: a method of adding a diimmonium compound according to the present invention to a powder or a pellet of the base resin, heating and melting it at 150 to 350° C., then molding it to produce a resin plate; or forming it into a film (into a resin plate) by using an extrusion machine. An amount of the diimmonium compound according to the present invention to be added to the base resin is ordinarily 0.01 to 30 mass %, preferably 0.03 to 15 mass % with respect to the total mass of the base resin, though the amount varies according to a thickness, absorption intensity and transmittance for visible light of the resin plate or the film to be produced.

The above described method (2) can employ a method of injecting a diimmonium compound according to the present invention, and a resin monomer or a prepolymer of the resin monomer into a mold (die) in the presence of a polymerization catalyst, and reacting them to cure the resin monomer or the prepolymer; or pouring the above substances into a die and solidifying them in the die into a hard product to mold them. Many resins can be molded with the method, but a specific example of the resin which can be applied to the molding method includes an acrylic resin, a diethylene glycol bis(allyl carbonate) resin, an epoxy resin, a phenol-formaldehyde resin, a polystyrene resin and a silicone resin. Among those, a method of bulk-polymerizing methyl methacrylate by casting is preferable, because it provides an acrylic sheet superior in hardness, heat resistance and chemical resistance. The concentration of the diiummonium compound according to the present invention in a resin varies according to the thickness, absorption intensity and transmittance for visible light of a resin plate or a film to be produced, but ordinarily is 0.01 to 30 mass %, preferably 0.03 to 15 mass % with respect to the total mass of the resin.

In the method, a well-known thermal radical polymerization initiator can be used as a polymerization catalyst. A specific example of the usable polymerization catalyst includes a peroxide such as benzoyl peroxide, p-chlorobenzoyl peroxide and diisopropyl peroxycarbonate; and an azo compound such as azobisisobutyronitrile. The content is normally 0.01 to 5 mass % with respect to the total mass of a mixture of a diimmonium compound and a resin monomer or a prepolymer of the resin monomer. A heating temperature in the thermal polymerization step is ordinarily 40 to 200° C., and a polymerization period of time is ordinarily 30 minutes to 8 hours. In addition to a thermal polymerization method, a method of adding a photoinitiator or a sensitizer to the resin and photopolymerizing the resin can be adopted.

The above described method (3) includes a method of preparing paint by dissolving a diimmonium compound according to the present invention in a resin (binder) and an organic solvent; and a method of fine-graining the diimmonium compound according to the present invention in the presence of a resin and dispersing it in water to prepare a water-based paint. The former method can employ, for instance, an aliphatic ester resin, an acrylic resin, a melamine resin, a urethane resin, an aromatic ester resin, a polycarbonate resin, a polyvinyl resin, an aliphatic polyolefin resin, an aromatic polyolefin resin, a polyvinyl alcohol resin, a polyvinyl modified resin, or a copolymer resin thereof, as a binder. When a diimmonium compound according to the present invention is employed in the method and is dissolved in a resin to be used as a binder even having a glass transition temperature (Tg) of a comparatively low Tg such as 70° C., the diimmonium compound does not cause denaturation, so that a coating layer superior in heat resistance and resistance to moist heat can be formed.

The former method also can use a halogen-based, alcohol-based, ketone-based, ester-based, aliphatic hydrocarbon-based, aromatic hydrocarbon-based or ether-based organic solvent, or a mixture thereof, as an organic solvent. The concentration of a diimmonium compound according to the present invention in a resin varies according to the thickness, absorption intensity and transmittance for visible light of a coating to be formed, but ordinarily is 0.1 to 30 mass % with respect to the total mass of the resin (binder).

A near-infrared light absorbing filter or the like can be obtained by applying a paint prepared as described above on a transparent resin film, a transparent resin plate or transparent glass with a spin coater, a bar coater, a roll coater, a spray gun or the like.

The above described method (4) can employ an adhesive for a resin such as a silicone resin, a urethane resin and an acrylic resin, or a well-known transparent adhesive for laminated glass such as a polyvinylbutyral adhesive and an ethylene-vinyl acetate adhesive, as a resin for a sticking material. A filter or the like is produced by adhesively bonding transparent resin plates with each other, a resin plate with a resin film, a resin plate with a glass plate, the resin films with each other, a resin film and a glass plate, and the glass plates with each other, with the use of the sticking agent which contains a diimmonium compound according to the present invention in an amount of 0.1-30 mass %.

In addition, in the above described methods (1) to (4), a normal additive to be used in molding a resin such as an ultraviolet absorbing agent and a plasticizing agent may be added in a kneading or mixing step.

The above described method (5) will be described later.

Thus obtained resin-molded article according to the present invention can be used in application fields such as a sheet or a film (near-infrared light absorbing filter) for absorbing near-infrared light, and a filter or a film required to cut infrared light such as a thermal insulation film, an optical article and sunglasses.

In the next place, a near-infrared light absorbing filter using a diimmonium compound according to the present invention will be described, which is the most characteristic use of the diimmonium compound according to the present invention.

A near-infrared light absorbing filter according to the present invention has only to have a layer containing a diimmonium compound according to the present invention, and accordingly may be the filter having a resin layer containing the diimmonium compound according to the present invention provided on a substrate, or may be a sheet, film, plate or layer of which the substrate in itself is formed of a resin composition (or a cured substance thereof) containing the diimmonium compound according to the present invention. The material for the substrate is not limited in particular as long as it can be generally used in a near-infrared light absorbing filter, but ordinarily a substrate of the above described resins or glass is employed. The thickness of the sheet, the film, the plate or the layer containing the diimmonium compound according to the present invention is ordinarily about 0.1 μm to 10 mm, and is appropriately determined according to an intended cutting rate for near-infrared light. The content of the diimmonium compound according to the present invention is also appropriately determined according to the intended cutting rate for the near-infrared light, as described above. The substrate to be used has preferably as high transparency as possible after having been formed and worked into a plate, a film or the like.

A near-infrared light absorbing filter according to the present invention may contain only one of diimmonium compounds shown by Formula (1) according to the present invention as a near-infrared light absorbing compound; it may be produced, however, by concomitantly using two or more of the diimmonium compounds according to the present invention; or it may be produced by concomitantly using the diimmonium compound according to the present invention and a near-infrared light absorbing compound other than the diimmonium compounds according to the present invention. The near-infrared light absorbing compound other than the diimmonium compounds according to the present invention includes, for instance, an organic compound such as a phthalocyanine-based compound, a cyanine-based compound and a dithiol nickel complex; a copper compound such as metallic copper, copper sulfide and copper oxide; a metal mixture containing zinc oxide as a main component; and a metallic compound or a mixture thereof such as a tungsten compound, indium tin oxide (ITO), and antimony-doped tin oxide (ATO).

For the purpose of adjusting a color tone of a near-infrared light absorbing filter, the filter may also contain a coloring matter (coloring matter for color matching) showing absorption in a visible light region in such a range as not to hinder an effect of the present invention. Alternatively, it is possible to prepare a filter containing only the coloring matter for color matching and then affix the near-infrared light absorbing filter according to the present invention to it.

When such a near-infrared light absorbing filter is used in a front plate of a plasma display, the filter needs to have as high transmittance for visible light as possible, and needs to have a transmittance of at least 40%, preferably at least 50%. The near-infrared light absorbing filter cuts near-infrared light in a region of 700 to 1,100 nm, and shows average transmittance of ordinarily 50% or less, preferably 30% or less, more preferably 20% or less and particularly preferably 10% or less, for the near-infrared light in said region.

A near-infrared light absorbing filter according to the present invention is an excellent near-infrared light absorbing filter which shows an extremely high transmittance in a visible light region, is friendly to the environment because of containing no antimony or arsenic, and absorbs the near-infrared light in a wide region. The filter is also superior in stability to a conventional near-infrared light absorbing filter which does not contain antimony but contains a perchlorate ion, a hexafluorophosphate ion and a fluoroborate ion. Furthermore, a diimmonium compound according to the present invention has sufficient solubility in a solvent to be used when the near-infrared light absorbing filter is produced, so that the filter has excellent producibility as well. The near-infrared light absorbing filter according to the present invention particularly has extremely superior heat resistance, resistance to moist heat and light resistance, hardly causes a reaction such as a decomposition reaction due to heat, and accordingly does not cause scarcely any coloration in a visible light region.

A near-infrared light absorbing filter using a diimmonium compound shown by Formula (1) according to the present invention may be produced by any of the above described methods (1) to (5); but preferably by the methods (3), (4) and (5); and particularly preferably by the method (5) which is a method of forming a sticking layer formed of a sticking agent containing the diimmonium compound according to the present invention, on the surface of a transparent support (when the transparent support has the above described function, on the surface of the side which does not hinder the function), in a step of coating the sticking agent, and making the sticking layer retain the diimmonium compound, because the method (5) shows a merit of cost reduction due to the reduction in the number of coating steps.

In the next place, a near-infrared light absorbing filter produced by adding a diimmonium compound represented by the Formula (1) according to the present invention to a sticking layer will be described in detail.

A diimmonium compound used in the present invention and represented by the Formula (1) may be singly contained in a sticking layer, but may be contained concomitantly with one or more near-infrared light absorbing compounds other than the diimmonium compound represented by Formula (1). An example of other concomitantly-usable near-infrared light absorbing compounds includes: the above described compounds; a diimmonium compound other than the diimmonium compound represented by Formula (1) according to the present invention; a nitroso compound or a metal salt thereof; an organic compound such as a cyanine-based compound, a squalirium-based compound, a thiol nickel complex salt, a phthalocyanine-based compound, a naphthalocyanine-based compound, a triarylmethane-based compound, a naphthoquinone-based compound and an anthraquinone-based compound; and an inorganic compound such as antimony tin oxide, indium tin oxide and a hexaboride compound of a rare earth metal like lanthanum hexaboride. As a matter of course, the diimmonium compound of Formula (1) may be used singly, or may be used in a form of a mixture with other one or more diimmonium compounds of Formula (1). When the diimmonium compound of Formula (1) is concomitantly used with another near-infrared light absorbing compound, 40 to 100 mass % of the diimmonium compound of Formula (1) according to the present invention is preferably contained in the mixture to be used.

In the next place, a method for preparing a near-infrared light absorbing filter will be described which contains a diimmonium compound of Formula (1) in a sticking layer.

A type and thickness of a support to be used for a near-infrared light absorbing filter according to the present invention is not limited in particular, as long as it has high transparency, has no flaw, and is endurable for use as an optical film. A specific example thereof includes a film of a polymeric resin such as a polyester-based (hereafter referred to as PET) resin, a polycarbonate-based resin, a triacetate-based resin, a norbornene-based resin, an acrylic resin, a cellulosic resin, a polyolefin-based resin and a urethane-based resin. It is also possible to use a transparent support containing an ultraviolet absorbing material for absorbing ultraviolet light coming from the outside to stabilize a function of an inner member such as a film. The surface of the support may be subjected to corona discharge treatment, plasma treatment, glow discharge treatment, roughening treatment or chemical treatment, or may have a coating layer of an anchor coat agent or a primer thereon, in order to improve its adhesiveness to a coating agent. The support is more preferably such a film or a sheet as to possess one or more functions among, for instance, reflection-reducing properties, antiglare/antireflection properties, antistatic properties, an antifouling property, neon light absorbing properties, electromagnetic-wave-shielding properties, color-tone-adjusting properties and the like, because when a sticking layer with the near-infrared light absorbing capability is formed on the support, the obtained optical filter can simultaneously possess the function imparted to the transparent support and the near-infrared light absorbing capability, and because such a form is advantageous in a production process and provides an excellent filter.

In the next place, an example of using a support (film) imparted with the above described functions will be described.

A first example is a reflection-reducing film which inhibits the reflection of light coming from the outside by coating the surface of a transparent support such as PET with a low refractivity agent together with a polymeric resin (binder) and other additives, or a film which acquires improved visibility by providing a hard coat layer and a high refractivity layer between the transparent support and the low refractivity layer, to control the reflected light from the respective layers so that they can cancel each other. A second example is an antiglare/antireflection film which acquires further improved visibility by adding finer particles into the high-refractivity layer or the other layers in the above described reflection-reducing film to irregularly reflect the light from the outside. The antiglare/antireflection film is easily commercially available from among brand names of Arctop series (Asahi Glass), Kayacoat ARS series (Nippon Kayaku Co., Ltd.), Kayacoat AGRS series (Nippon Kayaku Co., Ltd.) and ReaLook series (Nippon Oil & Fats).

A third example is an electromagnetic-wave-shielding film that includes a mesh type in which an ultrafine wire of a metal such as copper with a geometric form like a network is retained in a transparent support, and a thin film type in which an ultrathin film in such a range as to keep optical transparency is retained in the transparent support. However, a transparent electromagnetic-wave-shielding film of a mesh-type is preferably used as a support for a near-infrared light absorbing filter according to the present invention.

A transparent support having other function to be used in the present invention includes a film which has a single function or a plurality of functions concomitantly among neon light absorbing properties, ultraviolet light absorbing properties, antistatic properties, antifouling properties and color-tone-adjusting properties. The film can be prepared by a method well-known in itself such as a method of molding a resin composition containing a compound having the function.

A binder resin (hereafter referred to as a sticking material) which is a major component of a sticking layer is not limited in particular as long as it can uniformly disperse a diimmonium compound according to the present invention therein, can adhere to the surface of a transparent support while keeping transparency, and does not degrade the function of a filter. An example of a usable sticking material includes a sticking material of an acrylic-based resin, a polyester-based resin, a polyamide-based resin, a polyurethane-based resin, a polyolefin-based resin, a polycarbonate-based resin, a rubber-based resin and a silicone-based resin; and the sticking material of the acrylic-based resin is preferable because of being superior in transparency, adhesiveness and heat resistance. The sticking material of an acryl-based resin is formed by copolymerizing an alkyl acrylate having no functional group, which is a main component, with an alkyl acrylate having a functional group or a monomer component having a functional group other than the alkyl acrylate. A ratio of the alkyl acrylate having a functional group or the monomer component having a functional group other than the alkyl acrylate to be copolymerized is 0.1 to 20 parts by mass with respect to 100 parts by mass of the alkyl acrylate component having no functional group, and is preferably 1 to 10 parts by mass.

An example of an alkyl acrylate having no functional group includes an alkyl acrylate and an alkyl methacrylate with an alkyl group having 1 to 12 carbon atoms, such as methyl (meth)acrylate, ethyl (meth)acrylate, propyl (meth)acrylate, butyl (meth)acrylate, pentyl (meth)acrylate, hexyl (meth) acrylate, heptyl (meth)acrylate, octyl (meth)acrylate, nonyl (meth)acrylate, decyl (meth)acrylate, undecyl (meth)acrylate and dodecyl (meth)acrylate. Two or more of them may be concomitantly used, as needed.

A compound functioning as a cross-linking point with a crosslinking agent described below is used for an alkyl acrylate having a functional group or a monomer having a functional group other than the alkyl acrylate. A type of the compound is not limited in particular, but includes a (meth) acrylate monomer containing a hydroxyl group, such as 2-hydroxyethyl (meth)acrylate and hydroxypropyl (meth) acrylate; a (meth)acrylate monomer containing an amino group, such as N,N-dimethylaminoethyl acrylate and N-ter-butylaminoethyl acrylate; and acrylic acid and maleic acid. Two or more of them may be concomitantly used, as needed.

A sticking agent is preferably used as a composition which can cross-link a sticking material such as the above described acrylic resin by containing a crosslinking agent. The crosslinking agent is appropriately used in accordance with a type of the above described monomer. An example of the usable crosslinking agent includes: an aliphatic diisocyanate such as hexamethylene diisocyanate and trimethylolpropane adduct of hexamethylene diisocyanate; a polyisocyanate compound like an aromatic diisocyanate such as tolylene diisocyanate and trimethylolpropane adduct of tolylene diisocyanate; a melamine compound such as butyl-etherified styrol melamine and trimethylol melamine; a diamine compound such as hexamethylenediamine and triethyldiamine; an epoxy-resin-based compound such as bisphenol-A/epichlorohydrin; a urea-resin-based compound; and a metal salt such as aluminum chloride, ferric chloride and aluminum sulfate. The crosslinking agent is blended in an amount of ordinarily 0.005 to 5 parts by mass, preferably 0.01 to 3 parts by mass with respect to 100 parts by mass of the sticking material.

A sticking agent preferably includes an acrylic sticking material, for the reason of having excellent adhesion strength, an excellent cohesive power, high stability to light and oxygen because of containing no unsaturated bond in the polymer, and having a high degree of freedom for the selection of a type of a monomer and a molecular weight. The sticking material has preferably a high molecular weight (degree of polymerization) so as to keep adhesiveness to a transparent support. Specifically, the average molecular weight (Mw) of a main polymer is preferably about 600,000 to 2,000,000, more preferably about 800,000 to 1,800,000.

In a plasma display panel (PDP), a neon light absorbing filter made of a transparent support having a neon light absorbing compound retained thereon is ordinarily used for cutting an orange neon light with a wavelength of 550 to 620 nm, which originates from Ne gas generated when voltage is applied to the panel, inevitably decreases the color purity of a red light, and accordingly needs to be cut in front of the display to some extent. When a sticking layer containing a diimmonium compound according to the present invention is employed, the compound having neon light absorbing capability can be contained in the sticking layer. The sticking layer thereby obtained can simultaneously absorb near-infrared light and the neon light. Here, the neon light absorbing compound includes, for instance, an azaporphyrin compound such as tetraazaporphyrin compound, a cyanine compound, a squalirium compound, an azomethine compound, a xanthene compound, an oxonol compound and an azo compound.

When the compound is added into the sticking layer, the compound is preferably the tetraazaporphyrin compound because of having excellent heat resistance and resistance to moist heat.

An electromagnetic-wave-shielding filter also needs to be placed in front of a PDP, because an electromagnetic wave is emitted from the surface of the display, which is considered to be harmful to a human body from the view point of health. Accordingly, various types of the electromagnetic-wave-shielding filters are used, but a mesh type of the electromagnetic-wave-shielding filter is mainly used for the reason of having excellent electromagnetic-wave-shielding capability. The filter is made of a transparent support having ultrafine wires of a metal such as copper with a geometric form such as a network (mesh) retained thereon, as described above, is placed in front of the PDP, and prevents the harmful electromagnetic wave from leaking out to a viewer side by catching the harmful electromagnetic wave and dissipating it to the ground. However, the filter occasionally causes a problem of durability, because the mesh surface of the metal such as copper is retained by the transparent support in a state of contacting with air, though depending on the production method and the form, and accordingly when a sticking layer is applied onto the surface or the sticking layer is applied onto another functional film and the film is affixed to the surface through the sticking layer, the sticking layer causes discoloration mainly due to the oxidation of the metal such as copper. Effective methods for solving the problem are as follows:

(1) previously adding a rust-preventing agent for preventing the discoloration into the sticking layer; and (2) minimizing an amount of an organic acid in the sticking layer.

In addition, a mesh type of an electromagnetic-wave-shielding film occasionally degrades the transparency of the film, because it is produced by the steps of roughening the surface of a metallic foil such as copper in order to bond the copper foil to a transparent support with adequate adhesiveness, affixing the copper foil to the transparent support with an adhesive, and removing a part other than a grid line by dissolving the part with an etching technique while leaving only the grid line, and accordingly the rough surface shape of the copper foil is transferred onto the surface of a solidified adhesive layer coated on the transparent support and remains thereon. For this reason, the polymeric resin surface is further treated on the surface to make the surface smooth and the film transparent, but the transparence treatment is desirably omitted because the treatment causes increase in a cost. A sticking layer containing a rust-preventing agent is applied to the mesh-type of the electromagnetic-wave-shielding film having the grid surface of a metal such as copper (hereafter referred to as mesh surface) exposed to the outside, in other words, is applied to the electromagnetic-wave-shielding film having the transparence treatment not yet conducted. Then, it was found that the rough surface on the adhesive layer can be eliminated and the film becomes transparent by forming the sticking layer on the mesh surface or pressure-affixing a functional film on which the sticking layer is already formed to the mesh surface of the electromagnetic-wave-shielding film through the sticking layer. The method is a more rational method. In addition, the transparency of the adhesive layer increases as a refractive index of the sticking layer approaches to the refractive index of the surface-roughed adhesive layer, so that when the sticking agent is prepared, the refractive index needs to be considered so as to satisfy the above condition.

A rust-preventing agent to be used in the above described method (1) is not limited in particular as long as it has capability of preventing a metal from causing rust. A specific example of the usable rust-preventing agent includes 2-aminopyridine, 2-aminopyrimidine, 2-aminoquinoline, aminotriazin or aminotriazole and a substituted derivative thereof, a benzotriazole-based compound, phenyltetrazole and 2-aminotrithiazole. Among those, the benzotriazole-based compound is preferable, and 1H-benzotriazol is further preferable because of being easily handled. An amount of the rust-preventing agent to be used is 0.01 to 10 mass %, preferably 0.05 to 5 mass % with respect to a sticking layer after having been stuck and coated.

As for the above described method (2), it is preferable to control a content of an organic acid material of a monomer containing a carboxyl group such as acrylic acid and maleic acid to be used as a sticking material in a sticking layer to 0.5 mass % or less, by minimizing an amount of the used organic acid or adding a purification step, as needed.

A liquid sticking agent is prepared by sufficiently dissolving or dispersing a diimmonium compound of Formula (1) according to the present invention together with a sticking material, which is a main component of a sticking agent, a polymerization initiator, a crosslinking agent, an ultraviolet absorbing agent, a coloring matter for adjusting a color tone and other necessary additives in a solvent such as methyl ethyl ketone (MEK); and is coated onto the surface of a transparent support so that a layer thickness after having been dried becomes 5 to 100 μm, preferably 10 to 50 μm. The coating method is not limited in particular, and includes the methods of: applying the liquid sticking agent to a transparent support with a bar coater, a reverse coater, a comma coater or a gravure coater, and drying it to bond a sticking layer to the transparent support; and applying a liquid sticking agent to a mold-releasing film of a support with the bar coater, the reverse coater, the comma coater or the gravure coater, drying it and transferring the sticking layer to the transparent support. A near-infrared light absorbing filter according to the present invention is preferably designed so that a transmittance of near-infrared light having a wavelength of 700 to 1,100 nm can be 20% or less, more preferably 10% or less. An amount of the diimmonium compound according to the present invention to be contained in the sticking agent has only to match the above condition, and is ordinarily 1 to 20 mass % with respect to the sticking layer.

Next, an optical filter according to the present invention is obtained by stacking a near-infrared light absorbing filter according to the present invention, particularly having a near-infrared light absorbing film provided with a sticking layer containing the present diimmonium compound on a transparent support according to the present invention as an essential element, on a transparent support (film) having another function as will be described below. An optical filter according to the present invention may be attached to a front face of a PDP after having been previously bonded to a transparent glass plate or plastic sheet, or may be directly affixed to the front face of the PDP. The above described sticking layer has sufficient strength by only being pressure-bonded to glass or film, but it is also possible to increase the adhesive strength by pressure-bonding the sticking layer to the glass or film while heating it, as needed.

Examples of a transparent support having functions will be described below. In the examples, reference character NIR denotes near-infrared light, reference character Ne denotes neon light respectively, and a parenthesized part denotes a near-infrared light absorbing filter according to the present invention. As is clear from these configuration examples, it is understood that it is advantageous to make a sticking layer on a transparent support having a function such as a reflection-reducing transparent support contain a diimmonium compound of Formula (1) according to the present invention and a neon light absorbing compound.

(1) (reflection-reducing transparent support/NIR-Ne absorption-color adjustment sticking layer)/electromagnetic-wave-shielding film, (2) (reflection-reducing transparent support/NIR-color adjustment absorbing sticking layer)/electromagnetic-wave-shielding film/sticking layer/Ne absorbing film;

(3) reflection-reducing film/(NIR-Ne absorbing sticking layer/electromagnetic-wave-shielding transparent support);

(4) (antiglare-reflection-reducing transparent support/NIR-Ne absorbing polymeric resin layer)/electromagnetic-wave-shielding film;

(5) reflection-reducing film/(NIR-Ne absorbing-color adjustment sticking layer/PET transparent support)/sticking layer/electromagnetic-wave-shielding film;

(6) reflection-reducing film/(NIR-absorbing sticking layer/Ne-absorbing transparent support)/sticking layer/electromagnetic-wave-shielding film, (7) reflection-reducing film/sticking layer/electromagnetic-wave-shielding film/(NIR-absorbing-color adjustment sticking layer/Ne-absorbing transparent support);

(8) reflection-reducing film/sticking layer/electromagnetic-wave-shielding film/(NIR-Ne-absorbing sticking layer/PET transparent support)

Thus configured near-infrared light absorbing filter according to the present invention, which makes a sticking layer contain a diimmonium compound according to the present invention, is an excellent near-infrared light absorbing filter which shows an extremely high transmittance in a visible light region, does not contain antimony and arsenic, is friendly to the environment, and absorbs a near-infrared light in a wide region. The filter is also superior in stability to a conventional near-infrared light absorbing filter which does not contain antimony but contains a perchlorate ion, a hexafluorophosphate ion and a fluoroborate ion. Furthermore, a diimmonium compound according to the present invention has sufficient solubility in a solvent to be used when the near-infrared light absorbing filter is produced, so that the filter has excellent producibility as well. The near-infrared light absorbing filter according to the present invention particularly has extremely superior heat resistance, resistance to moist heat and light resistance, hardly causes a reaction such as a decomposition reaction due to heat, and accordingly almost does not cause coloration in a visible light region. Because of having such a characteristic, the near-infrared light absorbing filter according to the present invention can be singly used, but particularly is suitable for an optical filter for a plasma display.

In the next place, an optical information recording medium according to the present invention will be described.

An optical information recording medium according to the present invention has a recording layer on a substrate and is characterized in that the recording layer contains a diimmonium compound according to the present invention. The recording layer may be composed only of the diimmonium compound, or may be contained as a mixture composed together with various additives such as a binder. In this case, information is recorded by the diimmonium compound according to the present invention.

It is possible to improve the light resistance of the optical information recording medium by making a mixture containing a diimmonium compound according to the present invention and an organic coloring matter other than the diimmonium compound contained in a recording layer of the optical information recording medium which records information in the organic coloring matter. In such an optical information recording medium, the organic coloring matter provided for recording the information includes a cyanine-based pigment, a squalilium-based pigment, an indoaniline-based pigment, a phthalocyanine-based pigment, an azo-based pigment, a merocyanine-based pigment, a polymethine-based pigment, a naphthoquinone-based pigment and a pyrylium-based pigment. In such a method, an amount of the diimmonium compound according to the present invention to be used in the recording layer is ordinarily 0.01 to 10 mol, preferably 0.03 to 3 mol with respect to 1 mol of an organic coloring matter.

An optical information recording medium according to the present invention has a recording layer containing a diimmonium compound according to the present invention and a pigment other than the diimmonium compound provided on a substrate, and a reflective layer and a protective layer provided as well, as needed. A well-known substrate can be arbitrarily used for the substrate. The substrate includes, for instance, a glass plate, a metallic sheet, a plastic sheet and a film. A plastic resin for producing them includes an acrylic resin, a polycarbonate resin, a methacrylic resin, a polysulfone resin, a polyimide resin, an amorphous polyolefin resin, a polyester resin and a polypropylene resin. A shape of the substrate includes various shapes such as a disc shape, a card shape, a sheet shape and a rolled film shape.

A glass or plastic substrate may have a guide groove formed thereon so as to facilitate tracking during a recording step. The glass or plastic substrate may have an undercoating layer made from a plastic binder or an inorganic oxide and an inorganic sulfide provided thereon. The undercoating layer preferably has a coefficient of thermal conductivity lower than the substrate.

A recording layer in an optical information recording medium according to the present invention can be obtained by the steps of: dissolving, for instance, a diimmonium compound according to the present invention, and more preferably, the diimmonium compound according to the present invention and another organic coloring matter, into a well-known organic solvent such as tetrafluoropropanol (TFP), octafluoropentanol (OFP), diacetone alcohol, methanol, ethanol, butanol, methyl cellosolve, ethyl cellosolve, dichloroethane, isophorone and cyclohexanone; adding a binder, as needed; and applying the solution onto a substrate with a spin coater, a bar coater, a roll coater or the like. The recording layer can be also obtained by other methods such as a vacuum deposition method, a sputtering method, a doctor blade method, a casting method and a dipping method of dipping the substrate in the solution. In the above description, a usable binder includes an acrylic resin, a urethane resin and an epoxy resin and the like.

It is preferable for a recording layer to have a film thickness of 0.01 to 5 μm, more preferably 0.02 to 3 μm, in consideration of recording sensitivity and reflectance.

An optical information recording medium according to the present invention can provide an undercoating layer under the recording layer, a protective layer on the recording layer, and further a reflective layer between the recording layer and the protective layer, as needed. When the reflective layer is provided, the reflective layer is formed from gold, silver, copper and aluminum, and preferably a metal of gold, silver or aluminum. These metals may be singly used, or an alloy formed from two or more of the metals may be used. The layer is formed with a vacuum deposition method, a sputtering method, an ion plating method or the like. The reflective layer is formed into a thickness of 0.02 to 2 μm. The protective layer to be occasionally placed on the reflective layer is ordinarily formed by the steps of coating an ultraviolet-curing resin with a spin coating method; and irradiating it with ultraviolet light to cure the coated film. In addition to the above resin, an epoxy resin, an acrylic resin, a silicone resin, a urethane resin or the like is used for a material for forming a protective film. The protective film is ordinarily formed into a thickness of 0.01 to 100 μm.

Information is recorded or an image is formed on an optical information recording medium according to the present invention by irradiating a recording layer with a condensed high energy beam having a spot form of a laser such as a semiconductor laser, a helium-neon laser, a He—Cd laser, a YAG laser and an Ar laser, through a substrate or from an opposite side of the substrate. The information or the image is read out by irradiating the recording layer with a laser beam of a low power, and detecting a difference between the quantities of reflected lights from or transmitted lights through a pit-formed part and a pit-unformed part.

An optical information recording medium according to present invention has more excellent stability for light resistance than the optical information recording medium containing a conventional diimmonium compound. In addition, the diimmonium compound shown by Formula (1) according to the present invention has sufficient solubility in preparing the optical information recording medium, and has superior workability as well. When these compounds are contained, for instance, in a thin film of an organic coloring matter corresponding to a recording layer of the optical information recording medium, as a light stabilization agent, the compound also can remarkably improve the durability and stability for light resistance of the optical information recording medium, when replay is repeated.

EXAMPLES

In the next place, the present invention will be described in more detail with reference to Examples, but the present invention is not limited to these Examples. In addition, "part" and "%" in Examples are based on mass unless otherwise specified. In addition, in the following measured values for λmax, a difference of ±4 nm will be considered to be caused by measurement conditions and allowable.

Example 1

N,N,N',N'-tetrakis(p-di(n-butyl)aminophenyl)-p-phenylenediamine in an amount of 4 parts was added into DMF in an amount of 20 parts and dissolved therein while being heated to 60° C. Then, 8 parts of an aqueous solution containing 58.4% tris (trifluoromethylsulfonyl)methane (made by 3M Corporation) was added into the above liquid. Subsequently, 1.6 parts of silver nitrate dissolved in 23.5 parts of DMF was added to the liquid, and the resultant liquid was heated and stirred for 30 minutes. A diimmonium compound with a compound number of No. 1 in Table 1 in an amount of 7 parts was obtained by the steps of: filtering an undissolved substance out from the above liquid; adding water and methanol into the reaction liquid to precipitate crystals; filtering the precipitated crystals; washing them with methanol and then with water; and drying them.

λmax: 1,101 nm (dichloromethane), and molar absorptivity (ε): 107,000

Example 2

N,N,N',N'-tetrakis(p-di(iso-butyl)aminophenyl)-p-phenylenediamine in an amount of 6 parts was added into DMF in an amount of 36 parts, and was dissolved therein while being heated to 60° C. Then, 10.1 parts of an aqueous solution containing 58.4% tris (trifluoromethylsulfonyl)methane was added into the above liquid. Subsequently, 2.32 parts of silver nitrate dissolved in 35 parts of DMF was added to the liquid, and the resultant liquid was heated and stirred for 30 minutes. A diimmonium compound with a compound number of No. 2 in Table 1 in an amount of 8.4 parts was obtained by the steps of: filtering an undissolved substance out from the above liquid; adding water into the reaction liquid to precipitate crystals; filtering the precipitated crystals; washing them with methanol and then with water; and drying them.

λmax: 1,109 nm (dichloromethane), and molar absorptivity (ε): 107,000

Example 3

N,N,N',N'-tetrakis(p-di(n-propyl)aminophenyl)-p-phenylenediamine in an amount of 3 parts was added into DMF in an amount of 20 parts, and was dissolved therein while being heated to 60° C. Then, 6.7 parts of an aqueous solution containing 52% tris (trifluoromethylsulfonyl)methane was added into the above liquid. Subsequently, 1.4 parts of silver nitrate dissolved in 25 parts of DMF was added to the liquid, and the resultant liquid was heated and stirred for 30 minutes. A diimmonium compound with a compound number of No. 26 in Table 1 in an amount of 2 parts was obtained by the steps of: filtering an undissolved substance out from the above liquid; adding water and methanol into the reaction liquid to precipitate crystals; filtering the precipitated crystals; washing them with methanol and then with water; and drying them.

λmax: 1,098 nm (dichloromethane), and molar absorptivity (ε): 107,000

Example 4

N,N,N',N'-tetrakis(p-di(n-cyanopropyl)aminophenyl)-p-phenylenediamine in an amount of 5 parts was added into DMF in an amount of 30 parts, and was dissolved therein while being heated to 60° C. Then, 7.8 parts of an aqueous solution containing 58.4% tris (trifluoromethylsulfonyl) methane was added into the above liquid. Subsequently, 2.1 parts of silver nitrate dissolved in 30 parts of DMF was added to the liquid, and the resultant liquid was heated and stirred for 30 minutes. A diimmonium compound with a compound number of No. 3 in Table 1 in an amount of 5.4 parts was obtained by the steps of: filtering an undissolved substance out from the above liquid; adding water and methanol into the reaction liquid to precipitate crystals; filtering the precipitated crystals; washing them with methanol and then with water; and drying them.

λmax: 1,066 nm (dichloromethane), and molar absorptivity (ε): 110,000

Example 5

N,N,N',N'-tetrakis(p-diethylaminophenyl)-p-phenylenediamine in an amount of 2 parts was added into DMF in an amount of 20 parts, and was dissolved therein while being heated to 60° C. Then, 4.5 parts of an aqueous solution containing 58.4% tris (trifluoromethylsulfonyl)methane was added into the above liquid. Subsequently, 1.1 parts of silver nitrate dissolved in 20 parts of DMF was added to the liquid, and the resultant liquid was heated and stirred for 30 minutes. A diimmonium compound with a compound number of No. 21 in Table 1 in an amount of 0.8 parts was obtained by the steps of: filtering an undissolved substance out from the above liquid; adding water and methanol into the reaction liquid to precipitate crystals; filtering the precipitated crystals; washing them with methanol and then with water; and drying them.

λmax: 1,087 nm (dichloromethane), and molar absorptivity (ε): 101,000

Example 5A

N,N,N',N'-tetrakis(p-di(n-amyl)aminophenyl)-p-phenylenediamine in an amount of 3 parts was added into DMF in an amount of 40 parts, and was dissolved therein while being heated to 60° C. Then, 5.3 parts of an aqueous solution containing 52% tris (trifluoromethylsulfonyl)methane was added into the above liquid. Subsequently, 1.1 parts of silver nitrate dissolved in 30 parts of DMF was added to the liquid, and the resultant liquid was heated and stirred for 60 minutes. A diimmonium compound with a compound number of No. 5 in Table 1 in an amount of 1.9 parts was obtained by the steps of: filtering an undissolved substance out from the above liquid; adding water and methanol into the reaction liquid to precipitate crystals; filtering the precipitated crystals; washing them with methanol and then with water; and drying them.

λmax: 1,106 nm (dichloromethane), and molar absorptivity (ε): 108,000

Other compound examples can be prepared as in the case of the above described examples, by oxidizing corresponding phenylenediamine derivatives with an oxidizing agent in the presence of corresponding anions.

Example 6

A diimmonium compound with a compound number of No. 1 in Table 1 prepared in the above described Example 1 in an amount of 0.06 parts was dissolved in MEK (methyl ethyl ketone) in an amount of 0.94 parts. Into this solution, 3.4 parts of Folet GS-1000 (trade name of acrylic resin made by Soken Chemical & Engineering Corporation, and Tg: 100 to 110° C.) was added and mixed to form a coating solution. The solution was coated on Cosmoshine A4300 (trade name of polyester film made by Toyobo Corporation) into a thickness of 2 to 4 μm, and the coated film was dried at 80° C. Thus, a near-infrared light absorbing filter according to the present invention was obtained.

Near-infrared light absorbing filters according to the present invention were obtained by conducting the similar treatment by using diimmonium compounds respectively with a compound number No. 2 and a compound number No. 3 obtained in the above described Examples.

Example 7

A near-infrared light absorbing filter according to the present invention was obtained with the same method as in the case of Example 6 except that Folet GS-1000 (trade name of acrylic resin made by Soken Chemical & Engineering Corporation, and Tg: 100 to 110° C.) of a binder resin was changed to Acrydica LAL-115 (trade name of acrylic resin made by Dainippon Ink & Chemicals, Inc. and Tg: 70° C.), and that a diimmonium compound with a compound number No. 1 was changed to the diimmonium compound with a compound number No. 2 respectively.

Evaluation Test (1)

(Test for Stability of Heat Resistance)

Stability for heat resistance was tested by leaving each near-infrared light absorbing filter obtained in Example 6 and Example 7 in an oven of 100° C. for 480 hours. An amount of a remaining pigment was evaluated by measuring the change of absorbance in an absorption maximum wavelength of the filter before and after the test, with UV-3150 (trade name of spectral photometer made by Shimadzu Corporation).

Near-infrared light absorbing filter for comparison were prepared for comparison with the same method as in the case of Example 6 except that a diimmonium compound with a compound number No. 1 in Table 1 was replaced by hexafluoroantimonate of N,N,N',N'-tetrakis(p-di(n-butyl)aminophenyl)phenylene diimmonium (compound (A)), bis(trifluoromethanesulfonyl)imidate of N,N,N',N'-tetrakis(p-di(n-butyl)aminophenyl)phenylene diimmonium (compound (B)), bis(trifluoromethanesulfonyl)imidate of N,N,N',N'-tetrakis(p-di(cyanopropyl)aminophenyl)phenylene diimmonium (compound (C)), and bis(trifluoromethanesulfonyl) imidate of N,N,N',N'-tetrakis(p-di(i-butyl)aminophenyl)phenylene diimmonium (compound (D)). They were subjected to the same measurement. The result was shown in Table 2.

In addition, similar tests were tried with the use of hexafluoroantimonate of N,N,N',N'-tetrakis(p-di(cyanopropyl)aminophenyl)phenylene diimmonium and hexafluoroantimonate of N,N,N',N'-tetrakis(p-di(i-butyl)aminophenyl) phenylene diimmonium, but a near-infrared light absorbing filter in conformance with the above described case could not be prepared, because those compounds did not show sufficient solubility to the solvent.

TABLE 2

Test for stability of heat resistance

| | Compound | Pigment residual rate (%) Before test | After test |
|---|---|---|---|
| Example 6 | No. 1 | 100 | 80.1 |
| (Comparison) | (A) | 100 | 49.4 |
| (Comparison) | (B) | 100 | 32.3 |
| Example 6 | No. 2 | 100 | 87.2 |
| (Comparison) | (D) | 100 | 82.8 |
| Example 7 | No. 2 | 100 | 87.1 |
| Example 6 | No. 3 | 100 | 81.4 |
| (Comparison) | (C) | 100 | 53.5 |

It is understood from the result in Table 2 that a near-infrared light absorbing filter according to the present invention has a higher pigment residual rate and has more excellent resistance to a hot condition than a near-infrared light absorbing filter obtained by using a well-known diimmonium compound. It is also recognized from the result in Table 2 that the near-infrared light absorbing filter obtained even by using a sticking material with a comparatively low Tg shows excellent thermostability similar to the one obtained by using a sticking material with a comparatively high Tg.

Evaluation Test (2)

(Test for Stability of Resistance to Moist Heat)

Stability for resistance to moist heat was tested by using the same filter as the near-infrared light absorbing filter used in Evaluation Test (1), in the following way.

A near-infrared light absorbing filter according to the present invention obtained in Example 6 and Example 7 and a near-infrared light absorbing filter prepared for comparison were left in an environment of 60° C. and 90% RH (relative humidity) for 480 hours, and an amount of a remaining pigment was evaluated by measuring the change of absorbance in an absorption maximum wavelength of the filter before and after the test, with the above described spectrophotometer.

TABLE 3

Test for stability of resistance to moist heat

| | Compound | Pigment residual rate (%) | |
|---|---|---|---|
| | | Before test | After test |
| Example 6 | No. 1 | 100 | 79.6 |
| (Comparison) | (A) | 100 | 50.6 |
| (Comparison) | (B) | 100 | 56.5 |
| Example 6 | No. 2 | 100 | 88.0 |
| (Comparison) | (D) | 100 | 83.1 |
| Example 7 | No. 2 | 100 | 88.0 |
| Example 6 | No. 3 | 100 | 79.6 |
| (Comparison) | (C) | 100 | 52.4 |

It is understood from the result in Table 3 that a near-infrared light absorbing filter according to the present invention has a higher pigment residual rate and more excellent resistance to a high temperature and high humidity environment than a comparative example having the same substituent in a cation site. It is also recognized from the result in Table 3 that the near-infrared light absorbing filter obtained even by using a sticking material with a comparatively low Tg shows excellent stability to moist heat similar to the one obtained by using a sticking material with a comparatively high Tg.

Example 8

A film for absorbing near-infrared light and neon light was prepared by the steps of: preparing a uniform coating liquid in which respective materials for a sticking agent shown in the following Table 4 were mixed and dissolved; applying the coating liquid onto MRF-75 (trade name of mold-releasing PET film made by Mitsubishi Polyester Film Corporation with thickness of 75 μm) with a comma coater at 0.8 m/minute so as to form a sticking layer with a thickness of 18 μm; and drying the coated film at 110° C. The film was affixed to the reverse side of a reflection-reducing coat layer on Kayacoat ARS-D250-125 (trade name of reflection-reducing film made by Nippon Kayaku Co., Ltd.) of a transparent support, and the laminate was aged at 35° C. for two days to form a near-infrared light absorbing filter according to the present invention, which had reflection-reducing properties, near-infrared light absorbing properties, neon light absorbing properties and an adjusted color tone. Furthermore, the mold-releasing film of the filter was peeled and the rest film was affixed to the following electromagnetic-wave-shielding film 1 through the sticking layer to form an optical filter for a PDP which had a configuration of (reflection-reducing transparent support/NIR-Ne-absorbing and color-adjusting sticking layer)/electromagnetic-wave-shielding film 1, was easily produced and had superior optical performance.

TABLE 4

| Material | Amount of use |
|---|---|
| Diimmonium compound with compound number No. 2 | 1.0 part |
| TAP-2 (trade name of neon light absorbing agent made by Yamada Chemical Co., Ltd.) | 0.096 parts |
| Tinuvin 109 (trade name, UV absorber, made by Ciba-Geigy) | 1.2 parts |
| KAKASET Yellow GN (trade name of yellow coloring matter) | 0.006 parts |
| KAYASET Blue N (trade name of blue coloring matter) | 0.0072 parts |
| PTR-2500T (trade name of acrylic resin made by Nippon Kayaku Co., Ltd.) | 120.0 parts |
| M12ATY (trade name of curing agent made by Nippon Kayaku Co., Ltd.) | 0.324 parts |
| L45EY (trade name of curing agent made by Nippon Kayaku Co., Ltd.) | 0.444 parts |
| C-50 (trade name of curing agent made by Soken Chemical &Engineering) | 0.142 parts |
| Methyl ethyl ketone | 84.0 parts |

(Note)
TAP-2: tetraazaporphyrin compound; Tinuvin 109: benzotriazole-based compound; KAKASET Yellow GN: (color index) solvent yellow 93, made by Nippon Kayaku Co., Ltd.; KAYASET Blue N: (color index) solvent blue 35, made by Nippon Kayaku Co., Ltd.; M12ATY: metal chelate compound; L45EY: isocyanate compound; C-50: silane coupling agent;

(Preparation of Electromagnetic-Wave-Shielding Film 1)

An electromagnetic-wave-shielding film 1 having transparency was prepared by the steps of: laminating an electrolytic copper foil of a conductive material having a thickness of 18 μm and a rough surface onto Cosmoshine A-4100 (trade name of PET film made by Toyobo Corporation with thickness of 50 μm), through Nikaflex SAF (trade name of epoxy adhesive sheet, Nikkan Industries Co., Ltd., and 20 μm) of an adhesive layer so that the rough surface could contact with the epoxy adhesive sheet, and bonding them by heating at a condition of 180° C. and 30 kgf/cm$^2$; forming a copper grid pattern with a line width of 25 μm and a line spacing of 500 μm on the PET film of the obtained PET film provided with the copper foil, through photolithographic steps (resist film affixation-exposure-developing-chemical etching-resist film peeling); and coating an adhesive prepared by uniformly mixing an adhesive composition shown in the following Table 5 on the surface of the copper grid pattern so that the thickness of a dried coating could be about 40 μm, as transparence treatment.

TABLE 5

| Material | Amount of use |
|---|---|
| TBA-HME (trade name of polymeric epoxy resin made by Hitachi Chemical Corporation) | 100 parts |
| YD-8125 (trade name of Bisphenol A type epoxy resin made by Tohto Kasei Corporation) | 25 parts |
| IPDI (masked isocyanate, made by Hitachi Chemical Corporation) | 12.5 parts |
| 2-ethyl-4-methylimidazole | 0.3 parts |
| Methyl ethyl ketone | 300 parts |
| Cyclohexane | 15 parts |

Example 9

A near-infrared light absorbing filter according to the present invention, which has reflection-reducing properties, near-infrared light absorbing properties and neon light absorbing properties and contains a rust-preventing agent, was prepared by the same method as in the case of Example 8 except that the coating liquid was used which was prepared by adding 0.067 parts of a rust-preventing agent 1H-benzotriazole to raw materials for a sticking agent shown in Table 4, and sufficiently mixing them to dissolve them in a solvent. The mold-releasing film of the filter was peeled and the rest film was affixed to the mesh surface of the following electromagnetic-wave-shielding film 2 through the sticking layer to form an optical filter for a PDP which had a configuration of (reflection-reducing transparent support/NIR-Ne-absorbing and color-adjusting sticking layer)/electromagnetic-wave-shielding film 2, was easily produced and had superior optical performance.

(Preparation of Electromagnetic-Wave-Shielding Film 2)

An electromagnetic-wave-shielding film 2 having slightly inferior transparency was prepared by the steps of: laminating an electrolytic copper foil of a conductive material having a thickness of 18 μm and a rough surface onto Cosmoshine A-4100 (trade name of PET film made by Toyobo Corporation with thickness of 100 μm), through the above described Nikaflex SAF of an adhesive layer so that the rough surface could contact with an epoxy adhesive sheet, and bonding them by heating at a condition of 180° C. and 30 kgf/cm$^2$; and forming a copper grid pattern with a line width of 25 μm and a line spacing of 500 μm on the obtained PET film provided with the copper foil through photolithographic steps.

Example 10

A near-infrared light absorbing filter according to the present invention, which has reflection-reducing properties, near-infrared light absorbing properties and neon light absorbing properties and contains no organic acid in a sticking layer, was prepared by the same method as in the case of Example 8 except that an acrylic resin (trade name, PTR-2500T) in raw materials for a sticking agent shown in the above described Table 4 was changed to PTR-5500 (trade name, acrylate resin added with no organic acid, made by Nippon Kayaku Co., Ltd.). The mold-releasing film of the filter was peeled and the rest film was affixed to the mesh surface of the above described electromagnetic-wave-shielding film 2 through the sticking layer to form an optical filter for a PDP which had a configuration of (reflection-reducing transparent support/NIR-Ne-absorbing and color-adjusting sticking layer)/electromagnetic-wave-shielding film 2, was easily produced and had superior optical performance.

Example 11

A near-infrared light absorbing filter according to the present invention, which uses a PET film as a transparent support and contains a diimmonium compound with a compound number No. 2 in a sticking layer, was prepared by the same method as in the case of Example 8 except that raw materials other than a neon light absorbing agent, a yellow coloring matter and a blue coloring matter for a sticking agent shown in the above described Table 4 were used and Cosmoshine A4300 (trade name, PET film, made by Toyobo Corporation, and thickness of 100 μm) was used instead of Kayacoat ARS-D250-125.

Example 12

A near-infrared light absorbing filter according to the present invention, which uses a PET film as a transparent support and contains a diimmonium compound with a compound number No. 1 in a sticking layer, was prepared by the same method as in the case of Example 11 except that a diimmonium compound with a compound number No. 1 was used instead of a diimmonium compound with a compound number No. 2.

Comparative Example 1

A near-infrared light absorbing filter for comparison, which uses a PET film as a transparent support and contains a diimmonium compound shown by the following Formula (E) in a sticking layer, was prepared by the same method as in the case of Example 11 except that a diimmonium compound shown by the Formula (E) was used instead of a diimmonium compound with a compound number No. 2.

(E)

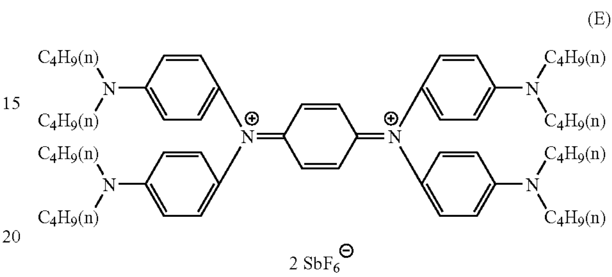

Comparative Example 2

A near-infrared light absorbing filter for comparison, which uses a PET film as a transparent support and contains a diimmonium compound shown by the following Formula (F) in a sticking layer, was prepared by the same method as in the case of Example 11 except that a diimmonium compound shown by the Formula (F) was used instead of a diimmonium compound with a compound number No. 2.

(F)

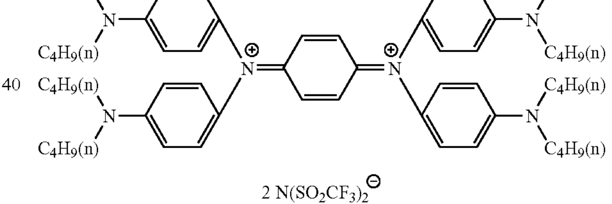

Comparative Example 3

A near-infrared light absorbing filter for comparison, which uses a PET film as a transparent support and contains a diiummonium compound shown by the following Formula (G) in a sticking layer, was prepared by the same method as in the case of Example 11 except that a diimmonium compound shown by the Formula (G) was used instead of a diimmonium compound with a compound number No. 2.

(G)

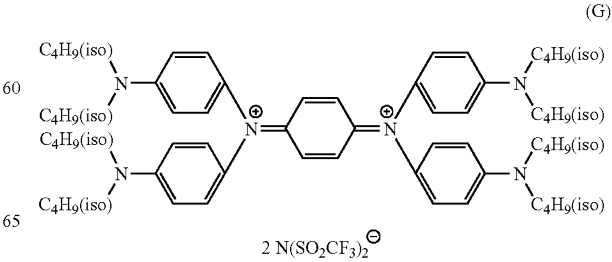

Evaluation Test (3)

(Test for Heat Resistance)

Heat resistance and resistance to moist heat were examined on each of near-infrared light absorbing filters according to the present invention, which use a PET film as a transparent support and were obtained in Example 11 to Example 12, and near-infrared light absorbing filters for comparison, which use a PET film as a transparent support and were obtained in Comparative Example 1 to Comparative Example 3.

It appears as a change of absorptivity characteristically for a visible light with a wavelength of 400 to 480 nm and a near-infrared light (wavelength of 700 to 1,100 nm), whether heat resistance and resistance to moist heat of diimmonium compound were deteriorated or not, so that the change of the absorptivity in these wavelength regions (three wavelengths were selected) was measured. Specifically, the heat resistance and the resistance to moist heat were examined by the steps of: affixing respective test pieces obtained in respective Examples and respective Comparative Examples to float glass with the thickness of 1 mm through a sticking layer; leaving them at 80° C. for 94 hours for a test of heat resistance, and in a thermostat-humidistat bath at 60° C. and 90% RH (relative humidity) for 94 hours for a test of resistance to moist heat, at rest; measuring the transmittance of light for the three wavelengths (430 nm, 880 nm and 980 nm) before and after the test; and observing an appearance of a sticking layer.

Table 6 and Table 7 show visual observation results for the appearance and the change of the transmittance in each wavelength (transmittance (%) after test−transmittance (%) before test in each wavelength).

TABLE 6

| | Test for heat resistance | | | |
|---|---|---|---|---|
| | Change (%) of transmittance | | | Result of evaluation of |
| | 430 nm | 880 nm | 980 nm | appearance |
| Example 11 | −1 | 1 | 0 | Pale brown and no change |
| Example 12 | −4 | 9 | 8 | Pale brown and slightly yellowish |
| Comparative Example 1 | 6 | 42 | 42 | Pale brown and little change |
| Comparative Example 2 | −15 | 5 | 4 | Change into pale yellow and occurrence of agglomeration and unevenness |
| Comparative Example 3 | −25 | 8 | 4 | Change into pale yellow green, and occurrence of unevenness and large amount of agglomerate |

TABLE 7

| | Test for resistance to moist heat | | | |
|---|---|---|---|---|
| | Change (%) of transmittance | | | Result of evaluation of |
| | 430 nm | 880 nm | 980 nm | appearance |
| Example 11 | −1 | 0 | 0 | Pale brown and no change |
| Example 12 | −4 | 9 | 9 | Pale brown and slightly yellowish |
| Comparative Example 1 | 4 | 48 | 47 | Pale brown and little change |
| Comparative Example 2 | −15 | 5 | 4 | Change into pale yellow and occurrence of agglomeration and unevenness |
| Comparative Example 3 | −25 | 8 | 4 | Change into pale yellow green, and occurrence of unevenness and large amount of agglomerate |

As is clear from results in Table 6 and Table 7, test pieces of Example 11 and Example 12 caused less unevenness in a sticking layer and showed less change in a wavelength of 430 nm than test pieces of Comparative Example 2 and Comparative Example 3, in both tests for heat resistance and resistance to moist heat, and consequently showed little change in appearance. In contrast to this, the test piece obtained in Comparative Example 1 showed a remarkable lowering of near-infrared light absorptance. In addition, a near-infrared light absorbing filter in Example 11 showed less transmittance change in each wavelength and less change in the appearance than the near-infrared light absorbing filter in Example 12.

What is claimed is:

1. A diimmonium compound represented by the following Formula (1):

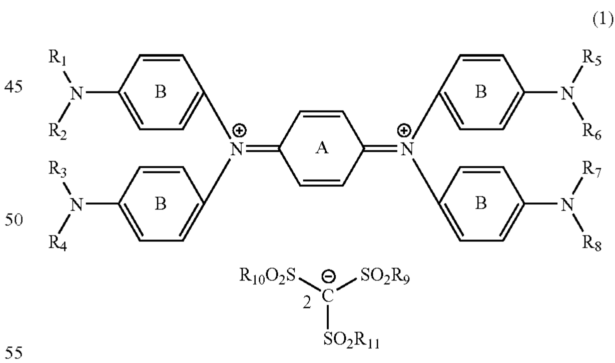

wherein $R_1$ to $R_8$ each independently represent a hydrogen atom or an aliphatic hydrocarbon residue which may have a substituent; $R_9$ to $R_{11}$ each independently represent an aliphatic hydrocarbon residue which may have a halogen atom; and rings (A) and (B) may independently have a further substituent.

2. The diimmonium compound according to claim 1, wherein the diimmonium compound shown by Formula (1) is a compound represented by the following Formula (2):

(2)

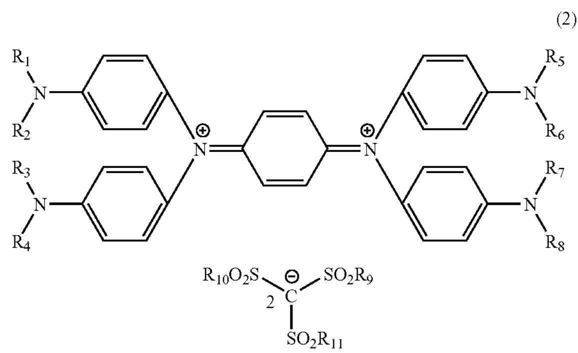

wherein $R_1$ to $R_8$ and $R_9$ to $R_{11}$ have the same meanings as described for Formula.

3. The diimmonium compound according to claim 1 or claim 2, wherein all of $R_9$ to $R_{11}$ in Formula (1) are aliphatic hydrocarbon residues having a fluorine atom.

4. The diimmonium compound according to claim 3, wherein the aliphatic hydrocarbon residue having a fluorine atom is a trifluoromethyl group.

5. The diimmonium compound according to claim 1, wherein all of $R_1$ to $R_8$ in Formula (1) are straight chain or branched chain alkyl groups.

6. The diimmonium compound according to claim 5, wherein the straight chain or branched chain alkyl group is a $C_1$ to $C_6$ straight chain or branched chain alkyl group.

7. The diimmonium compound according to claim 6, wherein the straight chain or branched chain alkyl group is a $C_2$ to $C_5$ straight chain or branched chain alkyl group.

8. The diimmonium compound according to claim 7, wherein the straight chain or branched chain alkyl group is an ethyl group, an n-propyl group, an n-butyl group, an iso-butyl group or an n-amyl group.

9. The diimmonium compound according to claim 1, wherein the substituents in aliphatic hydrocarbon residues which may have a substituent of $R_1$ to $R_8$ in Formula (1) or Formula (2) are each independently a halogen atom, a cyano group, a nitro group, a hydroxyl group, a carboxyl group, a carbonamide group, an alkoxycarbonyl group, an acyl group, an aryl group or an alkoxyl group.

10. The diimmonium compound according to claim 9, wherein all of $R_1$ to $R_8$ are alkyl groups substituted by a cyano group.

11. The diimmonium compound according to claim 10, wherein the alkyl group substituted by a cyano group is a cyanopropyl group.

12. A resin composition characterized by comprising the diimmonium compound according to claim 1 and a resin.

13. A near-infrared light absorbing filter characterized by having a layer comprising the diimmonium compound according to claim 1.

14. The near-infrared light absorbing filter according to claim 13, wherein the layer comprising the diimmonium compound is a sticking layer.

15. The near-infrared light absorbing filter according to claim 14, wherein the sticking layer comprises a rust-preventing agent.

16. The near-infrared light absorbing filter according to claim 15, wherein the rust-preventing agent is 1H-benzotriazole.

17. The near-infrared light absorbing filter according to claim 14, wherein the content of an organic acid in the sticking layer is 0.5 mass % or less with respect to the mass of the sticking layer.

18. The near-infrared light absorbing filter according to claim 14, characterized in that the sticking layer comprises a compound having the absorption maximum in a wavelength between 550 and 620 nm together with the diimmonium compound of Formula (1).

19. An optical filter for a plasma display panel characterized by comprising the near-infrared light absorbing filter according to claim 13 and an electromagnetic-wave-shielding layer.

20. A plasma display panel having the optical filter for a plasma display panel according to claim 19.

21. An optical information recording medium characterized by comprising a recording layer containing the diimmonium compound according to claim 1.

* * * * *